United States Patent [19]

Baum et al.

[11] 4,270,530

[45] Jun. 2, 1981

[54] TRACHEAL TUBE

[75] Inventors: Marcel Baum, Vienna, Austria; Horst Frankenberger, Bad Schwartau; Erik Schwanbom, Lübeck, both of. Fed. Rep. of Germany

[73] Assignee: Drägerwerk Aktiengesellschaft, Fed. Rep. of Germany

[21] Appl. No.: 86,949

[22] Filed: Oct. 22, 1979

[30] Foreign Application Priority Data

Nov. 3, 1978 [DE] Fed. Rep. of Germany ....... 2847681

[51] Int. Cl.³ .............................................. A61M 25/02
[52] U.S. Cl. ............................ 128/204.25; 128/207.15
[58] Field of Search ...................... 128/207.15, 207.14, 128/207.16, 207.17, 204.25, 205.24, 200.14, 200.18, 200.19, 349 B, 349 BV

[56] References Cited

U.S. PATENT DOCUMENTS

| | | | |
|---|---|---|---|
| 3,459,175 | 8/1969 | Miller | 128/349 B |
| 3,628,532 | 12/1971 | Magrath | 128/204.25 |
| 3,881,479 | 5/1975 | Carden | 128/207.15 |
| 4,030,492 | 6/1977 | Simbruner | 128/205.24 X |

FOREIGN PATENT DOCUMENTS 2226279 12/1973 Fed. Rep. of Germany ...... 128/204.25

*Primary Examiner*—Henry J. Recla
*Attorney, Agent, or Firm*—McGlew and Tuttle

[57] ABSTRACT

A tracheal tube comprises a hollow tube body having an open tube end and an inflatable sealing cuff disposed around the tube adjacent the tube end. At least one small diameter tube is associated with the hollow tube and it has a nozzle portion terminating in a discharge jet adjacent the open tube end for use in jet ventilation at high frequencies above 600 cycles per minute. The small diameter tube has a diameter of from between 0.4 to 0.05 × the inside diameter of the tube shaft and the outlet opening of the jet nozzle is arranged relative to the tube end either inside or outside the tube diameter at such a spacing that it is within ±5× the inside diameter of the tube body.

7 Claims, 3 Drawing Figures

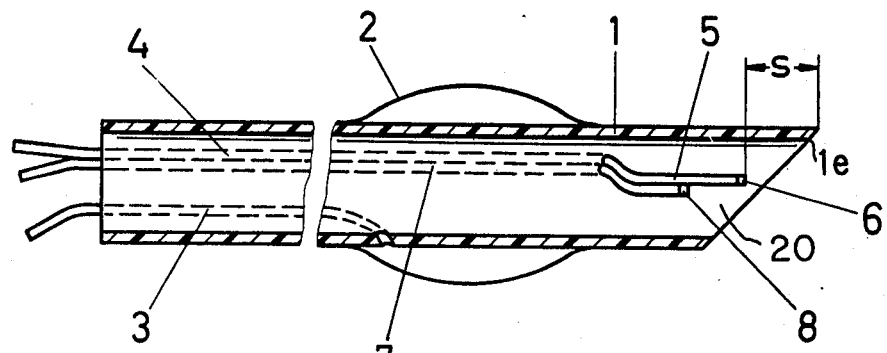
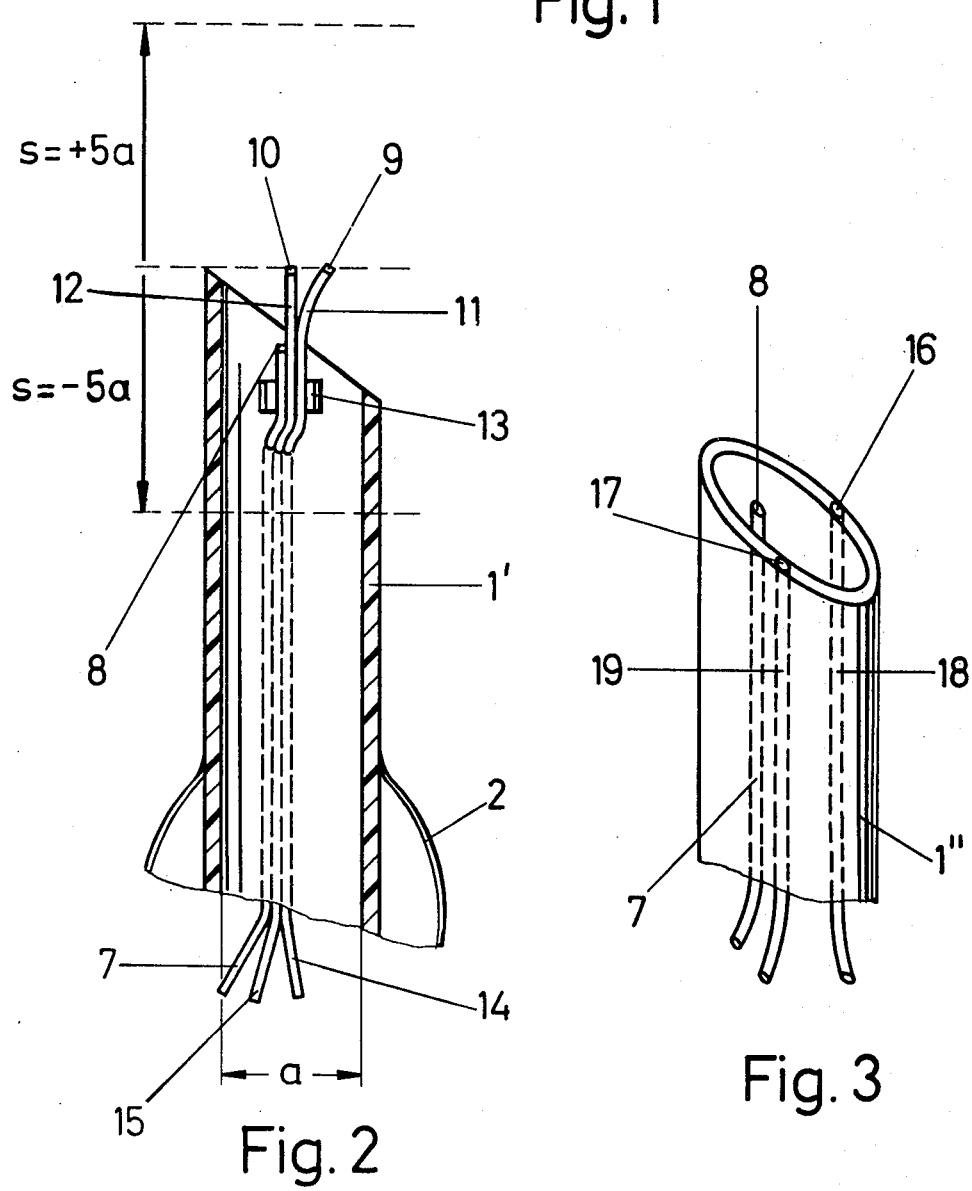

TRACHEAL TUBE

FIELD AND BACKGROUND OF THE INVENTION

This invention relates to tracheal devices in general and, in particular, to a new and useful tracheal tube having a tube shaft with an inflatable sealing cuff arranged in the range of the proximal end which is connected to a feed line extending in the range of the wall of the tube shaft.

For purposes of ventilation and to enhance breathing, it is known to use respirators which permit high frequency positive pressure ventilation (HFPPV). While the frequency of the known respirators controlled by the breathing rhythm is substantially in the normal physical range, breathing pulse sequence frequencies of up to 600 cycles per minute are used in HFPPV, with ratios of inspiration time to expiration time of 3:1 to 1:5.

The supply of the pulsating ventilation gas can be effected in a known manner either over a tracheal tube (A. Jonzon, G. Sedin and U. Sjoestrand: Acta anaesth. Scand. Supply. 53, 23–26, 1973), or directly over a catheter inserted into the trachea after puncturing the skin. (M. Klain, R. Brian Smith: "*Critical Care Medicine*", Vol. 5, No. 6, 280–287, 1977).

In the last-mentioned jet ventilation, the ventilation of test animals was effected at various ventilation rates from 20/cycles per minute to 200 cycles per minute with a minute volume of 17 liter per minute. The upper air passage remained in natural position without the inserted tracheal tube.

For effecting HFPPV, an insufflation and ventilation system is also known (U. Sjoestrand: Acta anaesth. Scand., Supply. 64, 14–15, 1977) wherein a ventilation attachment was placed on the tube shaft of an endotracheal tube, from which an insufflation catheter projects into the tube shaft. The breathing resistance against the interior of the attachment can be adjusted over a variable throttle opening.

Difficulties are encountered in ventilation with the presently known tracheal tubes if higher pulse sequence frequencies of the breathing pulses are to be used. The use of a jet catheter to supply the ventilation gas, which either projects freely into a tracheal tube or is introduced directly into the trachea, impairs the breathing considerably by turbulence which hinders the return flow and outflow of exhaled $CO_2$. The reason lies in the aerodynamically unfavorable, or inadequately fixed and defined, position of the jet nozzle relative to the widely branched hollow system of the lungs to be ventilated.

SUMMARY OF THE INVENTION

The present invention is based on the problem of designing a tracheal tube so that it is particularly suitable for jet ventilation at high frequencies. The effectiveness of the ventilating air supply to the lungs is to be improved, and favorable conditions are to be provided for the elimination of the exhaled $CO_2$ at low flow resistances. This problem is solved by providing at least one jet nozzle for use of the tracheal tube in jet ventilation at frequencies above 600 cycles per min. in the proximal end portion of the tracheal tube, whose diameter is between 0.4 to 0.5 times the inside diameter of the tube, and that the outlet orifice of the jet nozzle is arranged with regard to the proximal tube end inside or outside the tube shaft in a spacing distance which is within five times the inside diameter of the tube shaft. It was found, surprisingly, that these dimensioning specifications must be strictly observed if satisfactory flow conditions and low, substantially turbulent-free flow resistances are to be achieved. In order to avoid uncontrolled position changes, the jet nozzle must be properly fixed relative to the tube shaft.

Since the jet nozzle with its nozzle carrier and with the parts of the feed line projecting into the interior of the tube could hinder the introduction of other auxiliary instruments, such as suction probes, etc., a further advantageous development of the invention consists in that the jet nozzle is elastically mounted with the parts of the feed line protruding into the interior of the tube in such a way that the cross-section of the tube can be cleared again to a great extent. Additional auxiliary instruments can thus be introduced unhindered through the tube shaft. The reduced accessibility, caused by the detachable accessories compared to a free tracheal tube, is thus compensated to a great extent.

Though such a design seems generally advisable for detachable accessories fixed in a tube, it was found that the elastic support is of considerable importance when the above-described diameter or position specifications are to be realized for at least one jet nozzle in the proximal end portion of the tracheal tube. Since the jet nozzle must be properly fixed to achieve a favorable flow and return flow arrangement with regard to the interior of the tube shaft, this mostly results in a bulky arrangement in the interior, which would hinder the introduction of auxiliary instruments.

Another important improvement is achieved by arranging two jet nozzles spaced from each other, which are connected to separate feed lines. Such an arrangement permits selective ventilation of the lungs by gas currents adapted to the existing resistance conditions and the injury, respectively, (See J. M. Cavanilles; F. Garrigosa; E. Prist, J. R. Oncins: 7th Annual Scientific Symp. Soc. of *Critical Care Medicine,* Abstract 70, 1978). This design seems to be of particular advantage when using the given dimensioning specifications, but advantageously, it can also be used outside this range within the framework of a selective ventilation distribution circuit (SVDC). A favorable use of this nozzle arrangement is possible not only in the given frequency range above 600 cycles per minute, but also in lower frequency ranges.

The jet nozzle is preferably arranged in the vicinity of the central axis of the tube shaft. This provides favorable spreading possibilities for the issuing gas jet.

Since such a high-frequency ventilation must be carried out by means of a controlled jet ventilating gas source, it furthermore seems advisable to provide an additional test line whose mouth, either on the nozzle carrier, or in the range of the jet nozzle, is arranged upstream of the nozzle orifice, seen in the direction of the ventilating gas flow. In this position, the gas flow through the nozzle provides a certain shielding effect, which prevents clogging of the receiving opening of the test line.

The feed lines and the test line are preferably connected, at least in sections, with the wall of the tube shaft. When made of an elastic plastic, for example, complete or partial incorporation of the lines in the material of the tube shaft is advantageous.

For adaptation to the existing resistance conditions, it seems advisable if the jet nozzle has a variable cross-section. The variation can be achieved both by changing the nozzles or by varying the cross-sectional area of the nozzles.

Another important adjusting possibility in order to achieve optimum ventilation conditions and low flow resistances consists in making the jet nozzle adjustable in the longitudinal direction of the tube shaft. By connecting control devices, the effect of the ventilation can thus be monitored, and an optimum value can be set.

Accordingly, an object of the present invention is to provide a tracheal tube which comprises a hollow tube shaft or body having an open tube end with an inflatable sealing cuff disposed around the tube adjacent the tube end and which includes at least one small diameter tube associated with the hollow tube body, for example, by being embedded in the wall thereof, and which has a nozzle portion which terminates in a discharge jet adjacent the open tube end for use in jet ventilation at high frequencies above 600 cycles per minute and, wherein, the small diameter tube has a diameter of from 0.4 to 0.05 times the inside diameter of the tube body and that the outlet opening of the jet nozzle is arranged relative to the tube end either inside or outside the tube at a spacing such that it is within ±five times the inside diameter of the tube body.

A further object of the invention is to provide a tracheal tube which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWING

In the Drawing:

FIG. 1 is a partial axial sectional view of a tracheal tube for use with human beings, constructed in accordance with the invention, and substantially in the natural size;

FIG. 2 is a view similar to FIG. 1 of another embodiment of the invention, shown on a slightly enlarged scale; and FIG. 3 is a view similar to FIG. 1 of still another embodiment of the present invention.

DESCRIPTION OF THE PREFERRED EMBODIMENTS

Referring to the drawing in particular, the invention embodied therein, comprises, a tracheal tube, generally designated 1, for use with human beings, and having a longitudinal bore 20 which includes an open end 1e. FIG. 1 shows an endotracheal tube with a tube shaft 1 of an elastic plastic material. In the range of the proximal end of this tube, an inflatable sealing cuff 2 is arranged, which is connected to a feed line 3 embedded in the wall of tube 1.

As shown, the open end 1e of the tube shaft lies in a plane obliquely extending relative to the longitudinal axis of the tube shaft.

A feed line 4, which is also embedded in the wall of tube 1, projects in the proximal range from the inner wall and forms a nozzle carrier 5 whose outlet opening acts directly as a jet nozzle 6. Set back in the direction of flow of the ventilating gas, a test line 7 with a mouth 8 is arranged on nozzle carrier 5, for example, to monitor respiratory track pressure.

Jet nozzle 6 and mouth 8 of test line 7 are mounted properly and in fixed position in the range of the center axis of the tube shaft 1 by suitable selection of the material for the nozzle carrier 5.

The diameter of jet nozzle 6 is 1 mm, and is thus 0.09 times the inside diameter "a" of tube 1, which is fixed with 11 mm. The position of the jet nozzle determined by the distance "s" with regard to the proximal tube end 1e is $-0.7a$. In this embodiment, the jet nozzle is arranged inside of tube 1. The corresponding position in a longitudinal direction can be fixed, for example, by shortening the freely rising nozzle carrier 5 whose outlet opening is jet nozzle 6. The diameter of test line 7 is substantially equal to the diameter of feed line 4 to jet nozzle 6, and to the diameter of feed line 3 to sealing cuff 2.

The part of feed line 4 serving as nozzle carrier 5, together with test line 7, is so elastic with regard to the wall fastening, that jet nozzle 6 and the parts connected with it can be pushed aside, e.g., when a suction hose is introduced, so that the cross-section of the tube is substantially cleared.

In the embodiment according to FIG. 2, two jet nozzles 9 and 10 are provided which permit selective ventilation of the lungs. Over corresponding sections of feed lines 14 and 15, which are used as nozzle carriers 11 and 12, and which are displaceable in a holding part 13 secured on the wall, it is possible to adjust jet nozzles 9 and 10 in the longitudinal direction of tube 1 (jointly or individually). In some cases, it may be advisable to feed both jet nozzles 9 and 10 from a common feed line. Greater adaptability is achieved, however, if separate feed lines 14 and 15 are provided at least inside the tube or in its surface range. Test line 7 terminates in the direction of flow of the ventilating gas in front of the two jet nozzles 9 and 10 arranged for divergent gas currents.

The prescribed variation range for the distance "s" of the jet nozzles relative to the proximal tube end is indicated in the drawing by $+5a$ and $-5a$, where "a" denotes the inside diameter of the tube. In this embodiment, jet nozzles 9 and 10, arranged in the vicinity of the center axis of the tube 1 or their nozzle carriers 11 and 12, as well as the parts of feed lines 14 and 15 and the test line can likewise be deflected elastically toward the inner wall of the tube. The angular arrangement and longitudinal position of the two jet nozzles 9 and 10 can be checked by a corresponding scale division on the outer wall of the tube.

FIG. 3 shows a simplified embodiment of the tracheal tube 1" with two jet nozzles 16 and 17, whose discharges are substantially within the plane of the open end, having feed lines 18 and 19 are arranged completely inside the wall thickness of tube 1". Mouth 8 of test line 7 is set back correspondingly on the inner wall surface of tube 1" in the direction of flow of the ventilating gas. The other parts, not mentioned specifically, correspond to the embodiments of FIGS. 1 and 2. Such an embodiment of the tracheal tube is particularly simple to produce from a manufacturing standpoint.

While specific embodiments of the invention have been shown and described in detail to illustrate the application of the principles of the invention, it will be understood that the invention may be embodied otherwise without departing from such principles.

What is claimed is:

1. A tracheal tube comprising, a hollow tubular body having a bore with an open tube end, an inflatable sealing cuff disposed around said tubular body adjacent said tube end, at least one small diameter tube adjacent the wall of said hollow tubular body having a nozzle portion terminating in a discharge jet centrally within the bore adjacent said open tube end for use in jet ventilation at high frequencies above 600 cycles per minute, said small diameter tube having a diameter of between 0.4 to 0.05 times the inside diameter of said hollow tubular body, said discharge jet having a discharge opening which is fixed relative to the open end at a spacing having a dimension within five times the inside diameter of said hollow tubular body, and a test line adjacent the wall of said hollow tubular body alongside said small diameter tube having a portion extending out of the wall and terminating in an open mouth in the bore spaced upstream of said discharge jet.

2. A tracheal tube as set forth in claim 1 further comprising a feed line within said hollow tubular body having an open end through the wall adjacent said inflatable sealing cuff for inflating said inflatable sealing cuff.

3. A tracheal tube as set forth in claim 2 wherein said small diameter tube includes means for elastically supporting nozzle portion within said bore.

4. A tracheal tube as set forth in claim 3 wherein said elastic support means comprises a tubular nozzle carrier interconnecting said small diameter tube and said nozzle portion.

5. A tracheal tube comprising a hollow tubular body having an open tube end, an inflatable sealing cuff disposed around said tubular body adjacent said tube end, at least one small diameter tube at least partly embedded within the wall of said hollow tubular body having a nozzle portion terminating in a discharge jet adjacent said open tube end for use in jet ventilation at high frequencies above 600 cycles per minute, said small diameter tube having a diameter of between 0.4 to 0.05 times the inside diameter of said hollow tubular body, said discharge jet having a discharge opening which is in the plane of the open tube end, and a test line at least partly embedded within the wall of said hollow tubular body having a portion extending out of the wall and terminating in an open mouth on the inner surface of the wall upstream of said discharge jet.

6. A tracheal tube as set forth in claim 5 further comprising a feed line means at least partly embedded in the wall of said hollow tubular body having an open end through the wall adjacent said inflatable sealing cuff for inflating said inflatable sealing cuff.

7. A tracheal tube as set forth in claim 5 further wherein said open tube end is disposed in a plane extending obliquely relative to the longitudinal axis of said hollow tubular body, and each of said discharge opening of said discharge jet and said open mouth of said test line being disposed substantially in the plane of the open tube end.

* * * * *